United States Patent [19]

Witier

[11] Patent Number: 4,528,850
[45] Date of Patent: Jul. 16, 1985

[54] APPARATUS FOR MAKING DYNAMIC MEASUREMENTS OF SOLID SURFACE AREAS (SPECIFIC SURFACES) AND FOR DETERMINING THE ADSORPTION AND DESORPTION ISOTHERMS OF A GASEOUS MIXTURE OF CONSTANT COMPOSITION

[75] Inventor: Pierre Witier, Paris, France

[73] Assignee: Ministere de l'Urbanisme et du Logement of France, Paris, France

[21] Appl. No.: 606,754

[22] Filed: May 3, 1984

[30] Foreign Application Priority Data

May 18, 1983 [FR] France ............................... 83 08242

[51] Int. Cl.³ ...................... G01N 7/02; G01N 15/08
[52] U.S. Cl. ............................................... 73/432 PS
[58] Field of Search .................................. 73/432 PS

[56] References Cited

U.S. PATENT DOCUMENTS 3,211,006 10/1965 Haley, Jr. ............................ 73/432
3,211,007 10/1965 Atkins ............................ 73/432 PS
3,555,912 1/1971 Lowell ............................ 73/432 PS
3,850,040 11/1974 Orr, Jr. et al. ..................... 73/432

FOREIGN PATENT DOCUMENTS 1579273 8/1969 France.

Primary Examiner—S. Clement Swisher
Attorney, Agent, or Firm—Brumbaugh, Graves, Donohue & Raymond

[57] ABSTRACT

An apparatus applying the dynamic BET-type approach to the measurement of solid surface areas, allowing the pressure on the sample to be varied from a lower, subatmospheric value to a plurality of upper values either greater than or less than atmospheric pressure. Apparatus comprises, in the order of their appearance from upstream to downstream, the following parts: a source of a mixture of gaseous adsorbate and non-adsorbable gas, a pressure reducing valve, a reference circuit and a measurement circuit arranged in parallel, said measurement circuit incorporating a sample holding a cell and both said circuits going through a katharometer, then converging into a vacuum pump. A flow control valve is installed upstream from the sample holding cell and a throttling valve is inserted between said sample cell and the katharometer.

6 Claims, 1 Drawing Figure

U.S. Patent     Jul. 16, 1985     4,528,850
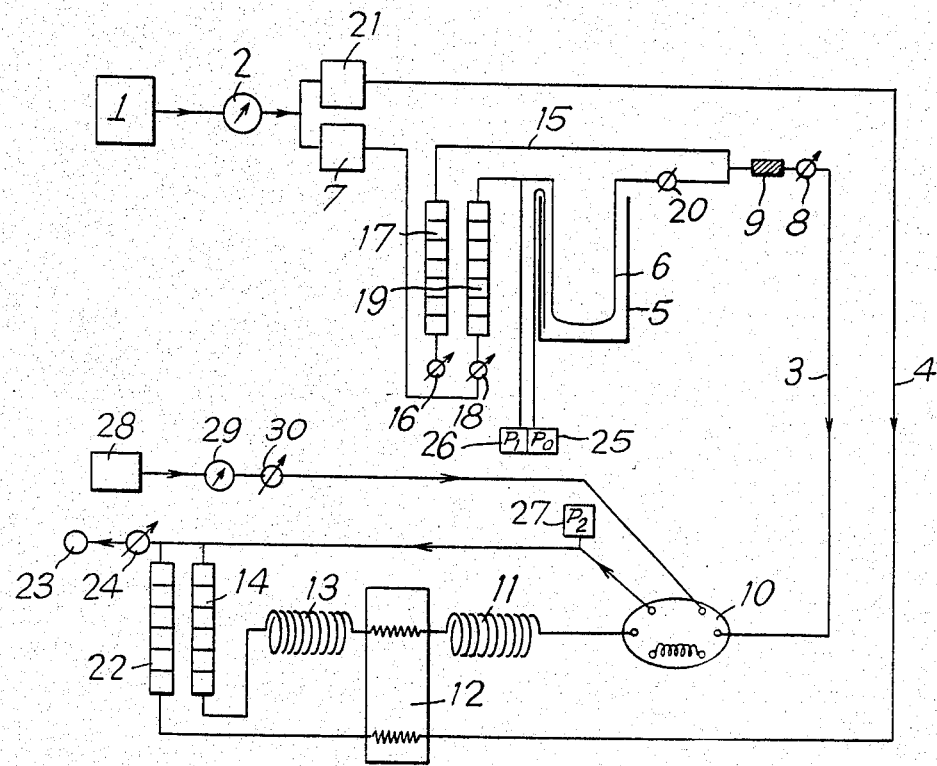

APPARATUS FOR MAKING DYNAMIC MEASUREMENTS OF SOLID SURFACE AREAS (SPECIFIC SURFACES) AND FOR DETERMINING THE ADSORPTION AND DESORPTION ISOTHERMS OF A GASEOUS MIXTURE OF CONSTANT COMPOSITION

This invention relates to the measurement of solid surface areas and the determination of complete adsorption and desorption isotherms using a dynamic BET-type constant composition gas method and apparatus.

Said method, named after Brunauer-Emmett-Teller, is known particularly from U.S. Pat. No. 3,211,006 and from a paper by Misters Pommier, Juillet and Teichner published in *Bulletin de la Societe Chimique de France*, No. 4 (1972) 1268–1273.

The apparatus disclosed in the latter paper comprises, from upstream to downstream: a source of a constant composition mixture of a non-adsorbable gas (helium) and of adsorbate (nitrogen), followed by a pressure reducer; and two parallel circuits—measurement circuit and a reference circuit—through a katharometer, i.e. a thermal conductivity cell. The measurement circuit further comprises a sample-holding cell, immersed in a Dewar flask; a six-way feed valve for calibrating the apparatus; and a flow controller.

The method and apparatus described in the aforementioned literature have contributed sustantially to the improvement of sensitivity and speed of measurement compared with the methods and equipment used previously.

It is the object of this invention to further improve the efficiency of this type of measurement, especially in terms of speed and accuracy.

To this effect, the invention provides a dynamic BET-type method whereby, in contrast to the method previously described, the pressure on the sample is made to vary between a lower, subatmospheric pressure and a plurality of uppers pressure values which may be less than or greater than atmospheric pressure.

This is accomplished by having both the measurement and the reference circuits or streams feed a vacuum pump.

Indeed, to determine a point of the adsorption isotherm by the dynamic BET method, the pressure must be set such that the product of said pressure times the concentration of adsorbate equals a predetermined value. In this way it is possible, for example, to determine the same point at a pressure of 0.2 MPa with a mixture of 5% adsorbate by volume as at 0.025 MPa with a mixture of 40% adsorbate by volume.

Working with an adsorbate-rich gaseous mixture, it is possible to significantly increase the speed of exchanges and thus to reduce the duration of the manipulations.

It is also possible to vary the pressure according to a given ratio (for example a ratio of 10:1) by using much lower maximum pressure values than those associated with an apparatus not using this technique.

The apparatus of the invention becomes even more efficient when, in an alternate embodiment, the flow controller of the measurement circuit is located upstream from the sample-holding cell and the total pressure on the sample is made to vary by means of a variable pressure drop obtained with a throttling valve (and preferably a needle valve) inserted betweem the cell and the katharometer.

In fact, as will be explained further on, it has been observed in accordance with the invention that the presence of a flow control valve between the adsorption cell and the katharometer, by introducing a "dead space" or holdup volume in the system, contributes to broadening the adsorption peaks recorded with the prior art devices.

It should be emphasized that in all the systems suggested heretofore the gas circuit incorporates a pressure reducer or a flow regulator between the cell where adsorption takes place and the katharometer circuit, both devices introducing a considerable holdup.

The use of a throttling valve between the sample-holding cell and the katharometer moreover affords a very small pressure drop between these two parts of the system and thus a very low minimum pressure in the adsorption cell.

Further advantages and features of the invention will become more readily apparent from the following description of one, non-limiting example of an embodiment of the apparatus according to the invention. Reference will be made throughout the description to the single appended FIGURE schematically illustrating the layout of said apparatus.

The FIGURE shows a source 1 of a constant composition gaseous mixture of, for example, an adsorbate such as nitrogen and a non-adsorbable gas such as helium. A pressure reducer 2 is placed after the source 1.

Two circuits, including a measurement circuit 3 and a reference circuit 4, are arranged in parallel. The measurement circuit 3 comprises a flow control valve 7 and a Dewar flask 5 containing liquid nitrogen into which the adsorption cell 6 can be immersed. A throttling valve 8 (preferably a needle valve), fitted with a protective filter 9, is placed downstream from said cell 6, followed by a conventional 6-way gas sampling valve 10, a first retarding coil or ballast 11, the filament katharometer 12, a second ballast 13 and a rotameter 14 to display the flow rate.

The measurement circuit 3 also comprises a sample cell bypass 15, said bypass branch 15 containing a needle valve 16 and a rotameter 17. The branch going through the sample cell 6 further comprises a needle valve 18 and a rotameter 19, upstream from the cell, as well as a downstream shutoff valve 20.

The reference circuit 4 is provided with a flow controller 21, the katharometer 12 and a rotameter 22.

The two circuits, i.e. the measurement circuit 3 and the reference circuit 4, converge to feed a vacuum pump 23 via another needle valve 24.

Three gauges 25, 26, 27 enable gauging of the pressures $P_0$ (nitrogen vapor saturation pressure), $P_1$ (total pressure on sample) and $P_2$ (pressure in the sampling loop).

A helium or nitrogen source 28 is connected to the sampling valve 10 via a pressure reducer 29 and a needle valve 30, to enable calibration of the detector through the operation of said sampling valve 10.

The apparatus operates as follows:

After setting the reference and measurement flows (say to 70 ml/min) by means of regultors 21 and 7, pressure in the katharometer circuit 12 is adjusted to a value $P_2$ (for example 0.012 MPa) by means of needle valve 24; the pressure in cell 6 is then adjusted with needle valve 8 to a selected value $P_1$. Value 8 is preferably fitted with a digital vernier control. This adjustment can be made manually or automatically, for example by servoing the needle valve 8 (motorized in this case) to the pressure gauge 26. The sample holder 6 is then immersed in the liquid nitrogen in vessel 5 and the adsorption peak at the corresponding pressure ($p_1$) is recorded; the stabilizing ballast 11, consisting of a long (say 5-meter), large-diameter (say 12 mm I.D.) tube, makes it possible to delay the appearance of the concentration signal at the katharometer 12 by some tens of seconds; the gas stream will have by that time resumed its initial flow rate, as required for an accurate measurement of the adsorbed or desorbed gas quantities to be made. The manipulation can then be continued by increasing the pressure $P_1$ to new levels $P'_1$, $P''_1$ and son on by working the needle valve 8 so as to cover the valid range of the BET rule or to obtain a complete isotherm; the pressure is then reduced, in stages again, to obtain the desorption isotherm.

The main advantage of the setup according to the invention over prior art devices lies, as previously suggested, in that in makes it possible to select a minimum working pressure for the sample cell which is less than atmospheric pressure, said minimum pressure being lowerable to the extent that the needle valve 8 allows a very small pressure difference to be maintained (of a few kPa) between the sample holder and the katharometer circuit. For example, pressures as low as 0.015 MPa can be had in the sample holder cell if the katharometer circuit is pressurized to 0.012 MPa; this accordingly reduces the maximum pressures required for developing the complete isotherm and makes it possible to increase the percentage of adsorbate in the adsorbate/non-adsorbable gas mixture—a particularly worthwhile possibility with respect to complete nitrogen isotherms (for large surface areas).

Moreover, the use of low pressures makes it possible to boost the speed of heat exchanges by allowing thin glass cells to be used, such as, for example, "U"-tubes which can be easily connected to "swaglock" type fittings. Said low pressures also afford greater safety.

A second advantage of the invention is that its pressure regulating system (needle valve 8) introduces only a very small holdup, on the order of a cubic centimeter or less, having a minimal broadening effect on the adsorption peaks, yet boosts sensitivity, accuracy and speed of measurement.

Regarding this matter, it should be noted that neither the ballast 11, nor the system's 3 mm to 4 mm diameter lines actually constitute dead spaces or holdups as construed hereinabove, i.e. in the sense of relatively large volumes entailing a significant broadening of the adsorption peak (such as that caused by a control valve or pressure reducing valve).

A further advantage of the invention is that the pressure changing system avoids flow surges between two successive measuring points, surges which in certain prior art devices sometimes project portions of the sample into the lines.

In one embodiment of the invention using a 40% nitrogen in helium mixture and a $P_0$ value (nitrogen vapor saturation pressure) of 0.1 MPa, an isotherm covering the $P/P_0=0.06$ to $P/P_0=1$ range can be determined by making $P_1$ vary from 0.015 to 0.25 MPa, absolute. The measurement of the solid surface ($P/P_0$ from 0.06 to 0.3) is made by varying pressure $P_1$ from 0.015 to 0.075 MPa, and a solid surface area measurement based on 4 points of the isotherm can be carried out in about 10 to 15 minutes on a silica gel (not including sample degassing time).

During adsorption, or during desorption for that matter, it is important not to exceed a certain limit of nitrogen concentration beyond which the katharometer 12 cannot provide a suitably liner response. For example, the nitrogen content should be kept within a 35% to 45% range. This requirement justifies the use of bypass circuit 15 (the dividing ratio whereof is adjustable through valves 16 and 18) around adsorption cell 6, especially for the first points of large surface area samples. Said bypass also makes it possible to isolate the cell during sample changing without interrupting the gas flow through the apparatus.

Another advantageous feature of the setup according to the invention is the second stabilizing ballast 13 (comparable to ballast 11) which can delay passage of a gas of modified composition through needle valve 24 while measurements are being made, to avoid the risk of causing variations (small as these might be) in the flow rate and in $P_2$. This ballast incidentally prevents a too strong flow of gas from entering the katharometer 12 and damaging its filaments at the time when the partial vacuum is being applied to the katharometer circuit.

What is claimed is:

1. A dynamic BET-type, constant composition gas apparatus for measuring solid surface areas and for determining complete adsorption and desorption isotherms, consisting, in the order of appearance of its parts from upstream to downstream, of a source of a gaseous adsorbate and non-adsorbable gas mixture, a pressure reducer, a reference circuit and a measurement circuit arranged in parallel, said latter circuit comprising a sample holding cell and both of said circuits going through a katharometer, wherein, after said katharometer, both of said circuits converge into a vacuum pump such that it is possible to vary the pressure on the sample from a lower subatmospheric value to a plurality of upper values either less than or greater than atmospheric pressure.

2. An apparatus as in claim 1, wherein a flow control valve is installed upstream from the sample holding cell and a throttling valve is installed between the sample cell and the katharometer.

3. An apparatus as in claim 2, wherein the measurement circuit includes a retarding coil or ballast located immediately upstream from the katharometer.

4. An apparatus as in claim 3, wherein a second ballast is provided immediately downstream from the katharometer.

5. An apparatus as in claim 1, wherein a bypass is provided around said sample cell, the flow within the bypass circuit being adjustable.

6. An apparatus as in claim 2, wherein said throttling valve is a needle valve.

* * * * *